United States Patent
Tu et al.

(10) Patent No.: US 10,617,473 B2
(45) Date of Patent: Apr. 14, 2020

(54) METHOD AND SYSTEM FOR EVALUATING FFR ON THE BASIS OF VIRTUAL STENT IMPLANTATION

(71) Applicant: PULSE MEDICAL IMAGING TECHNOLOGY (SHANGHAI) CO., LTD, Shanghai (CN)

(72) Inventors: Shengxian Tu, Shanghai (CN); Miao Chu, Shanghai (CN); Bo Xu, Shanghai (CN); Bing Liu, Shanghai (CN); Yazhu Chen, Shanghai (CN)

(73) Assignee: PULSE MEDICAL IMAGING TECHNOLOGY (SHANGHAI) CO., LTD, Shanghai (CN)

( * ) Notice: Subject to any disclaimer, the term of this patent is extended or adjusted under 35 U.S.C. 154(b) by 165 days.

(21) Appl. No.: 15/779,704

(22) PCT Filed: Nov. 4, 2016

(86) PCT No.: PCT/CN2016/104685
§ 371 (c)(1),
(2) Date: May 29, 2018

(87) PCT Pub. No.: WO2017/206438
PCT Pub. Date: Dec. 7, 2017

(65) Prior Publication Data
US 2018/0353241 A1    Dec. 13, 2018

(30) Foreign Application Priority Data

May 31, 2016   (CN) .......................... 2016 1 0379167

(51) Int. Cl.
*G06K 9/00*     (2006.01)
*A61B 34/10*    (2016.01)
(Continued)

(52) U.S. Cl.
CPC .............. *A61B 34/10* (2016.02); *A61B 6/504* (2013.01); *A61B 6/5217* (2013.01); *A61B 8/04* (2013.01);
(Continued)

(58) Field of Classification Search
None
See application file for complete search history.

(56) References Cited

U.S. PATENT DOCUMENTS

2011/0071404 A1*  3/2011  Schmitt ................ A61B 5/0066
                                                             600/479
2013/0090555 A1    4/2013  Kassab
(Continued)

FOREIGN PATENT DOCUMENTS

CN    103300820 A    9/2013
CN    103932694 A    7/2014
(Continued)

OTHER PUBLICATIONS

Ladisa et al ("Three-Dimensional Computational Fluid Dynamics Modeling of Alterations in Coronary Wall Shear Stress Produced by Stent Implantation", Annals of Biomedical Engineering, vol. 31, pp. 972-980, 2003 (Year: 2003).*

*Primary Examiner* — Shervin K Nakhjavan
(74) *Attorney, Agent, or Firm* — Muncy, Geissler, Olds & Lowe, P.C.

(57) ABSTRACT

A system for estimating post-virtual stenting fractional flow reserve (FFR) capable of: receiving geometrical parameters of a blood vessel segment, the geometrical parameters comprising first, second and third geometrical parameters; with a proximal end as a reference point, deriving a reference lumen diameter function and calculating a pre-virtual stenting percent diameter stenosis based on the above geometrical parameters and the distance from position along the segment to the reference point; receiving a virtual stenting
(Continued)

location; calculating a geometrical parameter of a virtual lumen of the post virtually-stented segment, deriving a post-virtual stenting geometrical parameter difference function and calculating a percent diameter stenosis based on the third geometrical parameter, the virtual stenting location and the reference lumen diameter function; taking derivative difference functions of the post-virtual stenting geometrical parameter difference function in multiple scales; and obtaining FFR based on the multiple scales of derivative difference functions and a maximum post-virtual stenting mean blood flow velocity. Post-virtual stenting FFR is estimated based on changes in percent diameter stenosis and the maximum mean blood flow velocity after virtual stent implantation using a multi-scale calculation method.

19 Claims, 3 Drawing Sheets

(51) Int. Cl.
| | | |
|---|---|---|
| *A61B 6/00* | (2006.01) | |
| *A61B 8/04* | (2006.01) | |
| *A61B 8/08* | (2006.01) | |
| *G16H 50/30* | (2018.01) | |
| *G06T 5/40* | (2006.01) | |
| *G06T 7/00* | (2017.01) | |
| *A61B 8/12* | (2006.01) | |
| *A61B 6/03* | (2006.01) | |

(52) U.S. Cl.
CPC .......... *A61B 8/0891* (2013.01); *A61B 8/5223* (2013.01); *G06T 5/40* (2013.01); *G06T 7/0012* (2018.01); *G16H 50/30* (2018.01); *A61B 6/03* (2013.01); *A61B 8/12* (2013.01); *A61B 8/481* (2013.01); *A61B 2034/104* (2016.02); *A61B 2034/105* (2016.02); *G06T 2207/30104* (2013.01)

(56) References Cited

U.S. PATENT DOCUMENTS

| | | | |
|---|---|---|---|
| 2013/0132054 A1* | 5/2013 | Sharma | G16B 5/00 |
| | | | 703/9 |
| 2014/0024932 A1 | 1/2014 | Sharma et al. | |
| 2014/0073976 A1 | 3/2014 | Fonte et al. | |
| 2015/0268039 A1 | 9/2015 | Tu et al. | |
| 2015/0374243 A1* | 12/2015 | Itu | G16H 50/50 |
| | | | 703/2 |
| 2016/0364860 A1* | 12/2016 | Taylor | A61B 5/026 |
| 2017/0364658 A1* | 12/2017 | Lavi | G16H 50/30 |

FOREIGN PATENT DOCUMENTS

| | | |
|---|---|---|
| CN | 104768465 A | 7/2015 |
| CN | 201510901329 | 12/2015 |
| CN | 105249954 A | 1/2016 |
| CN | 105326486 A | 2/2016 |

\* cited by examiner

METHOD AND SYSTEM FOR EVALUATING FFR ON THE BASIS OF VIRTUAL STENT IMPLANTATION

TECHNICAL FIELD

The present invention relates to methods and systems for use in the field of medical treatment and, in particular, in the estimation of an image-based pressure drop and fractional flow reserve (FFR) within a blood vessel segment after virtually stenting.

BACKGROUND

Fractional flow reserve (FFR) is an important technique for diagnosis of coronary function. FFR is defined as a ratio of the pressure distal to a stenosis relative to the pressure proximal to the stenosis during the maximal coronary blood flow (hyperemia) so as to reflect how the stenosis limits the maximum blood flow and can serve as a criterion for determining whether it will induce ischemia. A large number of clinical trials so far have provided adequate evidences indicating that FFR can be used to assess the functional significance of a stenotic lesion and in particular can provide important guidelines in the treatment plan selection for a critical stenotic lesion.

Invasive measurement of a blood pressure by means of pressure wire involves a significant amount of work and is associated with a risk of damaging the vessel. Patent Application No. CN201510901329.X, filed on Dec. 8, 2015, entitled "Method and System for Calculating Blood Vessel Pressure Difference and Fractional Flow Reserve (FFR)" discloses obtaining a pressure deviation within a blood vessel with lesions of different degrees of severity through computation in multiple scales based on a geometrical parameter and a blood flow velocity of the vessel obtained by coronary angiography. It is capable of properly distinguishing and evaluating the different impacts of geometric changes of a stenosed vessel with different degrees of severity on the blood flow pressure.

For a blood vessel with multiple degrees of stenosis, the location(s), size(s), number(s) and implantation order of stent(s) that is/are to be implanted are all of clinical interest. At present, no method has been developed for fast real-time prediction of the impact of stent implantation on FFR, which is, however, of great clinical significance.

To overcome the above problems, the inventors of the present invention, based on their previous work, i.e., Patent Application entitled "Method and System for Calculating Blood Vessel Pressure Difference and Fractional Flow Reserve (FFR)", as well as further inventive effort and improvement efforts, realized computation and assessment of a pressure drop and FFR within a virtually-stented blood vessel with lesions of different degrees of severity, which can help clinicians in the selection of a stenting strategy and assessment in prognosis.

SUMMARY OF THE INVENTION

It is an object of the present invention to provide methods and systems for estimating fractional flow reserve (FFR) based on virtual stent implantation.

Specifically, a method for estimating post-virtual stenting pressure drop within a blood vessel segment comprises: receiving geometrical parameters of a blood vessel segment comprising a proximal end and a distal end, wherein the geometrical parameters comprises a first geometrical parameter representing a cross-sectional area or diameter of the proximal end of the segment, a second geometrical parameter representing a cross-sectional area or diameter of the distal end of the segment, and a third geometrical parameter representing a cross-sectional area or diameter of an actual lumen at a first location between the proximal end and the distal end of the segment before virtual stenting; computing a reference lumen diameter at the first location of the segment based on the first geometrical parameter, the second geometrical parameter, the third geometrical parameter and a location data related to the first location; receiving a virtual stenting location defined by distances from proximal and distal ends of the virtual stent to the proximal end of the segment; computing a fourth geometrical parameter of a virtual lumen of the post virtually stented segment based on the third geometrical parameter, the virtual stenting location and the reference lumen diameter at the first location, the fourth geometrical parameter representing a cross-sectional area or diameter of the segment at the first location between the proximal end and the distal end after virtual stenting; receiving a pre-virtual stenting mean blood flow velocity of the segment; computing a pre-virtual stenting percent diameter stenosis at the first location based on the third geometrical parameter and the reference lumen diameter at the first location; computing a post-virtual stenting percent diameter stenosis and a post-virtual geometrical parameter difference at the first location based on the fourth geometrical parameter and the reference lumen diameter at the first location; obtaining a post-virtual stenting mean blood flow velocity by looking up a table listing relative blood flow velocities and their corresponding percent diameter stenosis based on the pre-virtual stenting mean blood flow velocity and the pre- and post-virtual stenting percent diameter stenosis; computing a post-virtual stenting pressure drop $\Delta P$ between a first blood flow pressure at the proximal end and a second blood flow pressure at the first location based on the post-virtual geometrical parameter difference at the first location, the post-virtual stenting mean blood flow velocity V and its square $V^2$.

Preferably, the method may further comprise: with the proximal end as a reference point, deriving a reference lumen diameter function based on the first geometrical parameter, the second geometrical parameter and a distance x from a certain position along the segment to the reference point, wherein the reference lumen diameter function represents reference lumen diameter at different positions along the segment as a function of the distance x from the position to the reference point.

Preferably, the derivation of the reference lumen diameter function may comprise a linear normalization as a function of location from the proximal end to the distal end of the segment.

Preferably, the method may further comprise: taking the proximal end as a reference point, computing the fourth geometrical parameter as a geometrical parameter of the post-virtually stented segment by the means of replacing the third geometrical parameter with the reference lumen diameter according to the virtual stenting location.

Preferably, the method may further comprise: with the proximal end as a reference point, based on the fourth geometrical parameter and the reference lumen diameter function, deriving a geometrical parameter difference function of the post-virtually stented segment which indicates a relationship of differences between the reference lumen diameter and the geometrical parameter of the virtual lumen of the segment (i.e., the fourth geometrical parameter) with respect to the distances x from the reference point.

Preferably, the method may further comprise: computing the pre-virtual stenting percent diameter stenosis DS % based on the third geometrical parameter and the reference lumen diameter function and computing the post-virtual stenting percent diameter stenosis DS %' based on the fourth geometrical parameter and the reference lumen diameter function. The percent diameter stenosis corresponds to the greatest degree of stenosis in the blood vessel segment.

Preferably, the method may further comprise: obtaining the post-virtual stenting mean blood flow velocity V' by looking up the table listing relative blood flow velocities and their corresponding percent diameter stenosis based on the pre-virtual stenting mean blood flow velocity V and the pre- and post-virtual stenting percent diameter stenosis DS %, DS %'. The table list the percent diameter stenosis and the corresponding relative blood flow velocities, wherein the relative blood flow velocities are normalized by blood flow velocity, with a maximum value of 1 and a minimum value of 0, independent of patient's specific blood flow velocity value.

Preferably, the method may further comprise: computing derivatives of the post-virtual stenting geometrical parameter difference function in n scales f1(x), . . . , fn(x), wherein the post-virtual stenting pressure drop ΔP between the first blood flow pressure and the second blood flow pressure is computed based on the n scales of derivative difference functions, and wherein the scales are resolutions indicative of distances between two adjacent points when calculating derivative numerically. The n scales may be a first scale, a second scale, . . . , and an n-th scale.

The derivative difference function f1(x) in the first scale may be adapted to detect a geometrical parameter difference between an actual lumen diameter and a reference lumen diameter caused by a first lesion characteristic.

The derivative difference function f2(x) in the second scale may be adapted to detect a geometrical parameter difference between an actual lumen diameter and a reference lumen diameter caused by a second lesion characteristic.

The derivative difference function fn(x) in the n-th scale may be adapted to detect a geometrical parameter difference between an actual lumen diameter and a reference lumen diameter caused by an n-th lesion characteristic. n may be a natural number greater than 1.

Preferably, the post-virtual stenting pressure drop ΔP between the first blood flow pressure and the second blood flow pressure may be calculated by weighting integrals of n scales of the derivative difference functions f1(x), , fn(x) and based on the post-virtual stenting mean blood flow velocity V and its square $V^2$.

Preferably, the post-virtual stenting pressure drop ΔP between the first blood flow pressure and the second blood flow pressure may be computed according to:

$$\Delta P = \alpha_1 [C_1 V + C_2 V^2] * \smallint f_1(x)dx + \alpha_2 [C_1 V + C_2 V^2] \smallint f_2(x)dx + \ldots + \alpha_n [C_1 V + C_2 V^2] * \smallint f_n(x)dx$$

where $C_1$ and $C_2$ represent coefficients of the post-virtual stenting mean blood flow velocity V and its square $V^2$, respectively, and $\alpha_1, \alpha_2, \ldots,$ and $\alpha_n$ denote weighted coefficients of the derivative difference functions f1(x), f2(x), . . . , fn(x) in the n scales, respectively.

Preferably, the location data related to the first location is a distance from the first location to the proximal end of the segment, and the mean blood flow velocity is a mean blood flow velocity within the proximal end to the distal end of the segment.

Preferably, the method may further comprise: receiving two-dimensional coronary angiography images captured under a certain angle; and registering region of interest of the images for different frames, wherein the region of interest of the coronary angiography is from the proximal end to the distal end of the vessel segment.

Preferably, the method may further comprise: plotting a gray-level histogram for the registered region of interest; and fitting the gray-level as a function of time within a cardiac cycle.

Preferably, the method may further comprise: obtaining a mean flow velocity of contrast medium from the gray-level fitting function.

Preferably, the pre-virtual stenting mean blood flow velocity V of the segment may be approximately equal to the mean flow velocity of the contrast medium obtained from the gray-level fitting function.

The present invention also provides a method for estimating post-virtual stenting fractional flow reserve (FFR) of a blood vessel, comprising:

receiving a pre-virtual stenting mean blood flow velocity V of a blood vessel segment under a resting state, optionally by conventional angiography (without maximum dilation of the microcirculation); obtaining a maximum pre-virtual stenting blood flow velocity $V_{max}$ under the condition of maximum dilation of microcirculation based on the mean velocity V; obtaining a post-virtual stenting maximum blood flow velocity $V'_{max}$ by looking up a table listing relative blood flow velocities and their corresponding percent diameter stenosis based on the pre-virtual stenting maximum blood flow velocity $V_{max}$ and pre- and post-virtual stenting percent diameter stenosis, wherein the relative blood flow velocities are normalized by blood flow velocity, with a maximum value of 1 and a minimum value of 0, independent of patient's specific blood flow velocity value; computing a pressure drop $\Delta P_{max}$ corresponding to the post-virtual stenting maximum blood flow velocity $V'_{max}$; and computing post-virtual stenting FFR according to FFR= (P1−$\Delta P_{max}$)/P1, wherein P1 represents a first blood flow pressure at a proximal end of a blood vessel segment, which can be approximately estimated by the cardiac diastolic and systolic pressures or accurately measured using a catheter.

Preferably, the method may further comprise: obtaining the pre-virtual stenting maximum blood flow velocity by looking up a correspondence table listing mean coronary blood flow velocities in a resting state and the corresponding maximum blood flow velocities under the condition of maximum dilation of microcirculation.

Preferably, the method may further comprise: obtaining the pressure deviation $\Delta P_{max}$ corresponding to the maximum blood flow velocity of a blood vessel segment using the method as defined above.

Preferably, FFR may be computed for a given fixed maximum blood flow velocity $V_{max}$.

The present invention also provides a system for estimating a post-virtual stenting pressure drop within a blood vessel segment, which can implement the methods as defined above. The system comprises: a geometrical parameter data acquisition module, configured to acquire geometrical parameters of a blood vessel segment having a proximal end and a distal end, the geometrical parameters comprising a first geometrical parameter representing a cross-sectional area or diameter of the segment at the proximal end, a second geometrical parameter representing a cross-sectional area or diameter of the segment at the distal end and a third geometrical parameter representing a pre-virtual stenting cross-sectional area or diameter of the segment at a first location between the proximal end and the distal end; a location data acquisition module, configured to acquire location data related to the first location; a reference lumen diameter computation module, configured to compute a reference lumen diameter of the segment related to the first location based on the first geometrical parameter, the second geometrical parameter, the third geometrical parameter and the location data of the first location; a virtual vascular lumen computation module, configured to receive a virtual stenting location and compute a fourth geometrical parameter as a geometrical parameter of virtual lumen of the post virtually stented segment based on the third geometrical parameter and the reference lumen diameter, and wherein the fourth geometrical parameter representing a cross-sectional area or diameter of the segment at the first location between the proximal end and the distal end after virtual stenting; a percent diameter stenosis computation module, configured to compute a pre-virtual stenting percent diameter stenosis at the first location based on the third geometrical parameter and the reference lumen diameter at the first location and compute a post-virtual stenting percent diameter stenosis at the first location based on the fourth geometrical parameter and the reference lumen diameter at the first location; a geometrical parameter difference computation module, configured to compute a geometrical parameter difference between the fourth geometrical parameter and the reference lumen diameter at the first location after virtual stenting; a velocity acquisition and computation module, configured to obtain a pre-virtual stenting mean blood flow velocity of the segment and obtain a post-virtual stenting mean blood flow velocity by looking up a table listing relative blood flow velocities and percent diameter stenosis; and a pressure drop computation module, configured to receive the post-virtual stenting geometrical parameter difference data at the first location output from the geometrical parameter difference computation module and the post-virtual stenting mean blood flow velocity V and its square $V^2$ output from the velocity acquisition and computation module and then to compute the post-virtual stenting pressure drop $\Delta P$ between a first blood flow pressure at the proximal end and a second blood flow pressure at the first location.

Preferably, the reference lumen diameter computation module may be configured to derive a reference lumen diameter function based on the first geometrical parameter, the second geometrical parameter and a distance x from position along the segment of vessel to the proximal end as a reference point, wherein the reference lumen diameter function is used to represent reference lumen diameter of different positions along the blood vessel as a function of distance x between the position and the reference point.

Preferably, the system may further comprise a normalization module configured to perform a linear normalization as a function of location from the proximal end to the distal end of the segment.

Preferably, the percent diameter stenosis may correspond to the most severe stenosis in the blood vessel segment.

Preferably, the geometrical parameter difference computation module may be configured to derive the geometrical parameter difference function at the first location after the virtual stenting based on the fourth geometrical parameter and the reference lumen diameter at the first location with the proximal end as a reference point, wherein the geometrical parameter difference function indicates a relationship of differences between the reference lumen diameter function and the geometrical parameter of the virtual lumen with respect to the distances x from the reference point.

Preferably, the system may further comprise a multi-scale derivative difference computation module configured to obtain derivatives of the post-virtual stenting geometrical parameter difference function in multiple scales.

Preferably, the pressure drop computation module may be configured to compute the post-virtual stenting pressure drop $\Delta P$ between the first blood flow pressure and the second blood flow pressure by weighting integrals of the derivative difference functions in the multiple scales obtained from the multi-scale derivative difference computation module and the post-virtual stenting mean blood flow velocity V and its square $V^2$ output from the velocity acquisition and computation module, wherein the multiple scales comprise two or more scales implemented as resolutions indicative of distances between two adjacent points when calculating derivative numerically.

Preferably, the system may further comprise a two-dimensional coronary angiography module configured to capture two-dimensional angiography of the segment under a certain angle and register region of interest of the images for different frames, wherein the region of interest of the coronary angiography is from the proximal end to the distal end of the vessel segment.

Preferably, the velocity acquisition and computation module may be configured to plot a gray-level histogram from the registered region of interest based on the output from the two-dimensional coronary angiography module, and fit the gray-level as a function of time within a cardiac cycle, from which a pre-virtual stenting mean flow velocity of contrast medium was obtained and then obtain the post-virtual stenting mean blood flow velocity through looking up the relative blood flow velocities and percent diameter stenosis table.

Preferably, the table may list percent diameter stenosis and their corresponding relative blood flow velocities and may be stored on the mean blood flow velocity acquisition and computation module or a separate storage module in the system. The present invention is not limited thereto. The relative blood flow velocities are normalized by blood flow velocity, with a maximum value of 1 and a minimum value of 0, independent of patient's specific blood flow velocity value.

The present invention also provides a system for estimating post-virtual stenting fractional flow reserve (FFR) in a blood vessel segment, comprising: a geometrical parameter data acquisition module, configured to acquire geometrical parameters of a blood vessel segment, the blood vessel comprising a proximal end and a distal end, wherein the geometrical parameters comprises a first geometrical parameter representing a cross-sectional area or diameter of the proximal end of the segment, a second geometrical parameter representing a cross-sectional area or diameter of the distal end of the segment and a third geometrical parameter representing a pre-virtual stenting cross-sectional area or diameter of the segment at a first location between the proximal end and the distal end; a location data acquisition module, configured to acquire location data related to the first location; a reference lumen diameter computation module, configured to derive a reference lumen diameter function with respect to a distance from a position on the segment to the proximal end as reference point; a reference lumen computation module, configured to compute a reference lumen diameter of the segment based on the above geometrical parameters and the distance to the proximal end, which is taken as a reference point; a virtual vascular lumen computation module, configured to receive a virtual stenting location and compute a fourth geometrical parameter as a geometrical parameter of virtual lumen of the post virtually stented segment based on the third geometrical parameter and the reference lumen diameter function, and wherein the fourth geometrical parameter representing a cross-sectional area or diameter of the post virtually stented segment at the first location between the proximal end and the distal end; a percent diameter stenosis computation module, configured to compute a pre-virtual stenting percent diameter stenosis at the first location based on the third geometrical parameter and the reference lumen diameter at the first location and compute a post-virtual stenting percent diameter stenosis at the first location based on the fourth geometrical parameter and the reference lumen diameter at the first location; a geometrical parameter difference computation module, configured to derive a geometrical parameter difference function of the post virtually stented segment based on the reference lumen diameter function and the fourth geometrical parameter; a multi-scale computation module, configured to obtain derivatives of the post-virtual stenting geometrical parameter difference function in multiple scales, wherein the scales are resolutions indicative of distances between two adjacent points when calculating derivative numerically; a mean blood flow velocity acquisition and computation module, configured to acquire a mean blood flow velocity of the segment by conventional coronary angiography and obtain a post-virtual stenting mean blood flow velocity through looking up a table listing relative blood flow velocities and percent diameter stenosis; a maximum mean blood flow velocity computation module, configured to obtain a post-virtual stenting maximum mean blood flow velocity of the segment by looking up a correspondence table stored on this module; and an FFR computation module, configured to obtain post-virtual stenting FFR as a ratio of a second blood flow pressure at the first location to a first blood flow pressure at the proximal end of the segment based on the post-virtual stenting multi-scale of derivative difference functions and the maximum mean blood flow velocity.

Preferably, the table list percent diameter stenosis and their corresponding relative blood flow velocities and may be stored on the mean blood flow velocity acquisition and computation module or a separate storage module in the system. The relative blood flow velocities are normalized by blood flow velocity, with a maximum value of 1 and a minimum value of 0, independent of patient's specific blood flow velocity value.

Preferably, the maximum blood flow velocity acquisition module may be configured to obtain the maximum blood flow velocity by looking up the correspondence table listing mean coronary blood flow velocities in a resting state and corresponding maximum blood flow velocities under the condition of maximum dilation of microcirculation. The correspondence table may be stored on the maximum blood flow velocity acquisition module or a separate storage module in the system.

The present invention offers the following benefits: on the basis of "Method And System For Calculating Blood Vessel Pressure Difference And Fractional Flow Reserve", it realizes computation and assessment of a pressure drop and fractional flow reserve (FFR) within a virtually-stented blood vessel with lesions of different degrees of severity, which can help clinicians in the selection of a stenting strategy and assessment of prognosis.

BRIEF DESCRIPTION OF THE DRAWINGS

In order to make the embodiments of the present invention and conventional technical solutions to be more apparent, the accompanying drawings for facilitating their description will be briefed below. Obviously, the drawings present merely several embodiments of the invention, and person of ordinary skill in the art may obtain other drawings based on the following set forth without exerting any inventive effort.

DETAILED DESCRIPTION

Figure 1A:
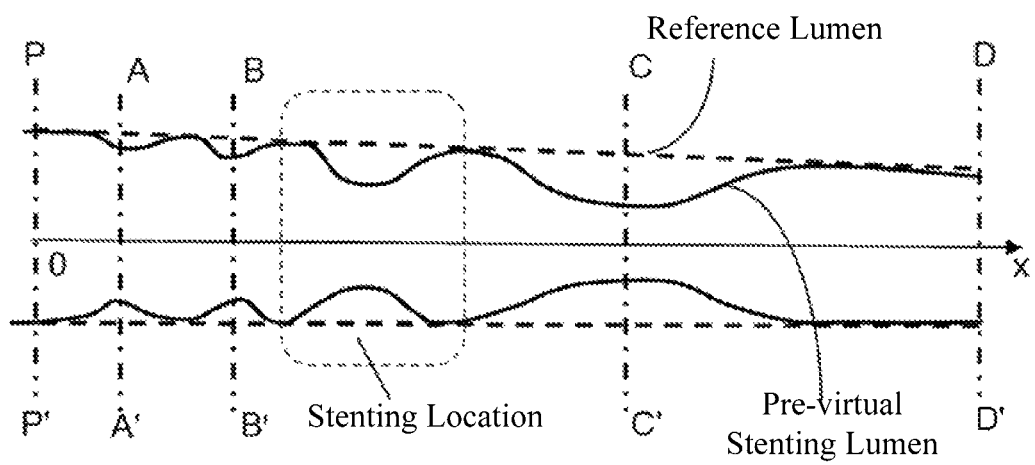
FIG. 1A schematically illustrates a structural comparison between an actual lumen of a blood vessel prior to virtual stenting and its reference lumen of the present invention.

A method and system for recommending an application according to embodiments of the present invention with be described in detail below with reference to the accompany drawings. It is to be noted that the embodiments set forth below are only some, but not all embodiments of the inventions. All other embodiments made by those of ordinary skill in the art based on the embodiment disclosed herein without exerting any inventive effort will fall within the scope of the invention.

It is to be understood by those skilled in the art that, the following specific embodiments or examples of the present invention are provided as a number of optimized arrangements for further explaining the subject matter of the invention rather than limiting the scope of the invention in any sense. Unless otherwise expressly specified that one or more of the specific embodiments or examples cannot be combined with another or other specific embodiments or examples, the arrangements are intended to be able to be combined or associated with one another.

Embodiment 1

The present invention provides a method for estimating a pressure drop within a blood vessel after implanting a virtual stent, which comprises: receiving geometrical parameters of a blood vessel segment, the blood vessel comprising a proximal end and a distal end, the geometrical parameters comprising a first geometrical parameter representing a cross-sectional area or diameter of the proximal end of the segment, a second geometrical parameter representing a cross-sectional area or diameter of the distal end of the segment and a third geometrical parameter representing a cross-sectional area or diameter of an actual lumen of a first location of the segment between the proximal end and the distal end before virtual stenting; computing a reference lumen diameter of the segment at the first location based on the first geometrical parameter, the second geometrical parameter, the third geometrical parameter and a location data related to the first location; receiving a virtual stenting location defined by distances from proximal and distal ends of the virtual stent to the proximal end of the blood vessel; computing a fourth geometrical parameter of a virtual lumen of the post-virtual stenting segment based on the third geometrical parameter, the virtual stenting location and the reference lumen diameter, the fourth geometrical parameter representing a cross-sectional area or diameter of the post-virtually stented segment at the first location between the proximal end and the distal end; receiving a pre-virtual stenting mean blood flow velocity of the segment;

with the proximal end as a reference point, based on the first geometrical parameter, the second geometrical parameter and a distance x from a position along the segment to the reference point, deriving a reference lumen diameter function used to represent reference lumen diameter of different positions along the blood vessel as a function of the distance x from the position to the reference point.

In a specific embodiment, the computation of the reference lumen diameter function comprises a linear normalization as a function of location from the proximal end to the distal end.

In a specific embodiment, with the proximal end as a reference point, the fourth geometrical parameter is computed as the geometrical parameter of the post-virtually stented segment by the means of replacing the third geometrical parameter with the reference lumen diameter according to the virtual stenting location.

In a specific embodiment, with the proximal end as a reference point, based on the fourth geometrical parameter and the reference lumen diameter function, a geometrical parameter difference function of the post virtually stented segment is derived as a function indicating a relationship of differences between the reference lumen diameter function and the geometrical parameter of the virtual lumen of the segment (i.e., the fourth geometrical parameter) with respect to the distances x from the reference point.

In a specific embodiment, a pre-virtual stenting percent diameter stenosis DS % is computed based on the third geometrical parameter and the reference lumen diameter function, and a post-virtual stenting percent diameter stenosis DS %' is computed based on the fourth geometrical parameter and the reference lumen diameter function. The percent diameter stenosis DS % and DS %' both correspond to the most severe stenotic lesion of the blood vessel segment before and after the virtual stent implantation.

In a specific embodiment, a post-virtual stenting mean blood flow velocity V is obtained by looking up a table listing relative blood flow velocities and their corresponding percent diameter stenosis based on the pre-virtual stenting mean blood flow velocity V and the pre- and post-virtual stenting percent diameter stenosis DS %, DS %'. The table lists percent diameter stenosis and their corresponding relative blood flow velocities that are normalized by flow velocity, with a maximum value of 1 and a minimum value of 0, independent of patient's specific blood flow velocity values.

In a specific embodiment, derivatives of the post-virtual stenting geometrical parameter difference function in n scales, wherein the post-virtual stenting pressure drop ΔP between the first blood flow pressure and the second blood flow pressure is computed based on the n scales of derivatives. The scales are resolutions indicative of distances between two adjacent points when calculating derivative numerically, and the n scales consist of a first scale, a second scale, . . . , and an n-th scale.

The first scale of derivative difference function f1(x) is adapted to detect a geometrical parameter difference between an actual lumen diameter and a reference lumen diameter caused by a first lesion characteristic, ignoring other lesion characteristics.

The second scale of derivative difference function f2(x) is adapted to detect a geometrical parameter difference caused by a second lesion characteristic.

The n-th scale of derivative difference function fn(x) is adapted to detect a geometrical parameter difference caused by an n-th lesion characteristic wherein n is a natural number greater than 1.

In a specific embodiment, the post-virtual stenting pressure drop ΔP between the first blood flow pressure and the second blood flow pressure may be obtained by weighting integrals of the derivative difference functions f1(x), . . . , fn(x) in the n scales as well as the post-virtual stenting mean blood flow velocity V and its $V^2$.

Preferably, the post-virtual stenting pressure drop ΔP between the first blood flow pressure and the second blood flow pressure may be computed according to:

$$\Delta P = \alpha_1[C_1V + C_2V^2]*\int f_1(x)dx + \alpha_2[C_1V + C_2V^2]\int f_2(x)dx + \ldots + \alpha_n[C_1V + C_2V^2]*\int f_n(x)dx$$

where C1 and C2 represent coefficients of the post-virtual stenting mean blood flow velocity V and its square $V^2$, respectively, and $\alpha_1, \alpha_2, \ldots$, and $\alpha_n$ denote weighted coefficients for the derivative difference functions f1(x), f2(x), . . . , fn(x) in the n scales, respectively.

Preferably, the location data related to the first location is a distance from the first location to the proximal end of the segment, and the mean blood flow velocity of the segment is a mean blood flow velocity within the proximal end to the distal end of the segment.

In a specific embodiment, two-dimensional coronary angiography images are received under a certain angle, and images registration is performed on the regions of interest for different frames, wherein the region of interest of the coronary angiography is from the proximal end of the vessel segment to and the distal end.

Preferably, the method may further comprise: plotting a gray-level histogram for the registered region of interest; and calculating the gray-level fitting function with respect to time changes within a cardiac cycle.

Preferably, the method may further comprise: obtaining a mean flow velocity of contrast medium within the segment of vessel based on the gray-level fitting function.

Preferably, the pre-virtual stenting mean blood flow velocity V within the segment of vessel is approximately equal to the mean flow velocity of the contrast medium obtained from the gray-level fitting function.

The method will be described in further detail below with reference to FIGS. 1 to 3. Referring to FIG. 1A, the method includes: receiving geometrical parameters of a segment of a blood vessel, including: (a) a geometrical parameter (cross-sectional area or diameter) at a proximal end P of the segment; (b) a geometrical parameter (cross-sectional area or diameter) at a distal end D of the segment; and (c) taking P as a reference point, obtaining a geometrical parameter (cross-sectional area or diameter) of the segment between P and D as well as the distance x from the position of the segment to the reference point P.

The geometrical parameters may be obtained by any of a variety of techniques including two-dimensional or three-dimensional coronary angiography, coronary computed tomography angiography (CTA), intravascular ultrasound (IVUS) or optical coherence tomography (OCT). Generally, the geometrical parameters of the segment may be its cross-sectional areas or diameters. In case of two-dimensional diameters of the blood vessel being received, the cross-sections of the blood vessel can be assumed to be circular and its cross-sectional areas can be thus obtained.

Based on these data (a), (b) and (c), a reference geometrical parameter of the segment (i.e., assuming there was no lesion) can be obtained as a linear function of the distance from the reference point P. In FIG. 1, the solid lines represent an actual lumen of the segment, while the dotted lines represent a reference lumen thereof.

Figure 1B:
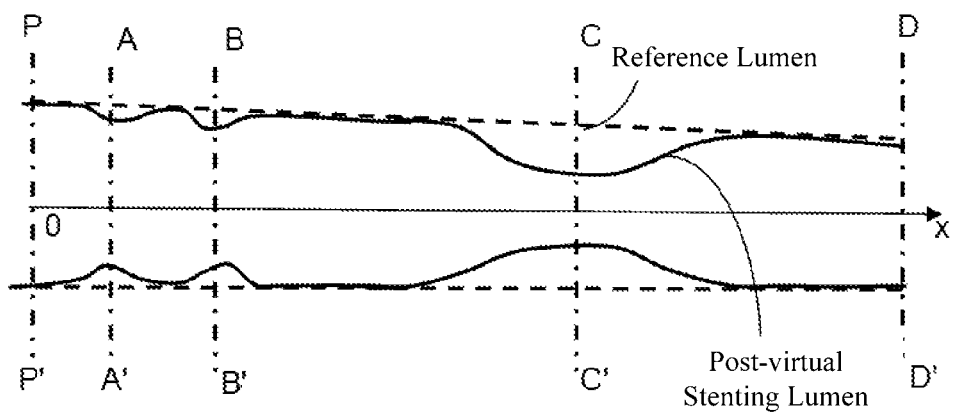
FIG. 1B schematically illustrates a structural comparison between the actual lumen after a virtual stent implantation and its reference lumen of the present invention.

After receipt of a virtual stenting location, a fourth geometrical parameter representing a post-virtual stenting cross-sectional area or diameter of the segment at the first location between the proximal end and the distal end can be obtained by replacing the geometrical parameter (cross-sectional area or diameter) (c) with that of the reference lumen as a linear function of the distance from the reference point P. In FIG. 1B, the solid lines represent a post-virtual stenting lumen of the blood vessel.

Figure 2:
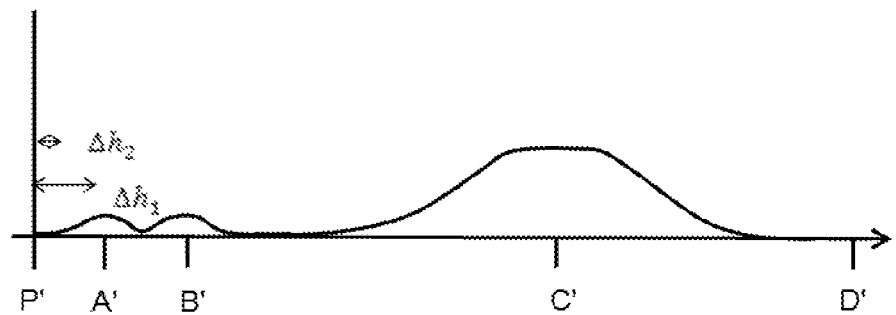
FIG. 2 is a diagram schematically showing a difference function representing a geometrical parameter difference between the actual lumen after virtual stenting and the reference lumen in accordance with the present invention.

FIG. 2 is a diagram showing the geometrical parameter difference between the post-virtual stenting actual lumen and the reference lumen as a geometrical parameter difference function F(x). It is noted that, as revealed by an analysis, an accurate pressure deviation between a first blood flow pressure and a second blood flow pressure can be calculated using the geometrical parameter difference function F(x) in a single scale in the case of a single type of lesion. However, when multiple types of lesions, especially including a diffuse lesion, coexist in the blood vessel, the pressure deviation calculated by the method will suffer from a significant error. On the one hand, when the single scale is small, the derivative difference function at severe stenosis will be close to that at mild stenosis. This will lead to underestimation of the impact of the severe stenosis on the pressure deviation. On the other hand, when the single scale is great, the derivative difference function at the mild stenosis will be zero, i.e., failure to detect the impact of the mild stenosis on the pressure deviation.

In order to overcome the deficiencies of the conventional methods of a single scale, it is preferred to take derivative of the geometrical parameter difference in n scales for a blood vessel with different degrees of lesions, and calculate the pressure deviation between the first and second blood flow pressures based on derivative difference functions in these scales.

For example, in a preferred embodiment, derivatives of the geometrical parameter difference function are derived in two scales, and the pressure deviation between the first and second blood flow pressures is calculated from these two scales of derivatives difference functions (including a first greater scale and a second smaller scale). The derivative difference function f1(x) in the first scale is adapted to detect a geometrical parameter difference between an actual lumen diameter and a reference lumen diameter caused by long severe lesion, with geometrical parameter differences caused by focal stenosis being ignored. The derivative difference function f2(x) in the second scale is adapted to detect a geometrical parameter difference caused by a focal change of the segment.

Derivatives of the difference function f(x) of FIG. 2 are taken in these two scales.

The derivative difference function in the greater scale is:

$$f_1(x) = \frac{F(X + \Delta h_1/2) - F(X - \Delta h_1/2)}{\Delta h_1}$$

and the derivative difference function in the smaller scale is:

$$f_2(x) = \frac{F(X + \Delta h_2/2) - F(X - +\Delta h_2/2)}{\Delta h_2}$$

where $\Delta h_1 > \Delta h_2$.

Figure 3A:
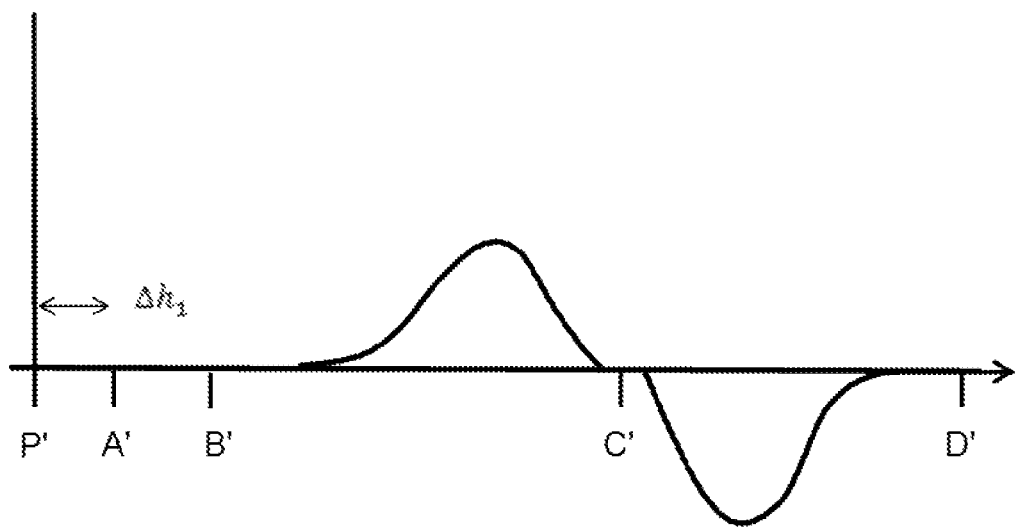
FIG. 3A is a diagram showing a derivative difference function f1(x) in a first scale.
Figure 3B:
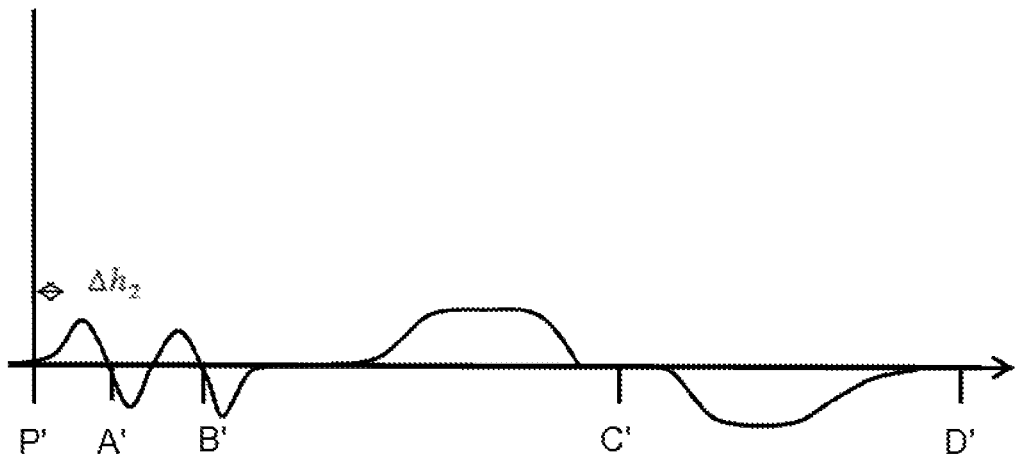
FIG. 3B is a diagram showing a derivative difference function f2(x) in a second scale.
Figure 4:
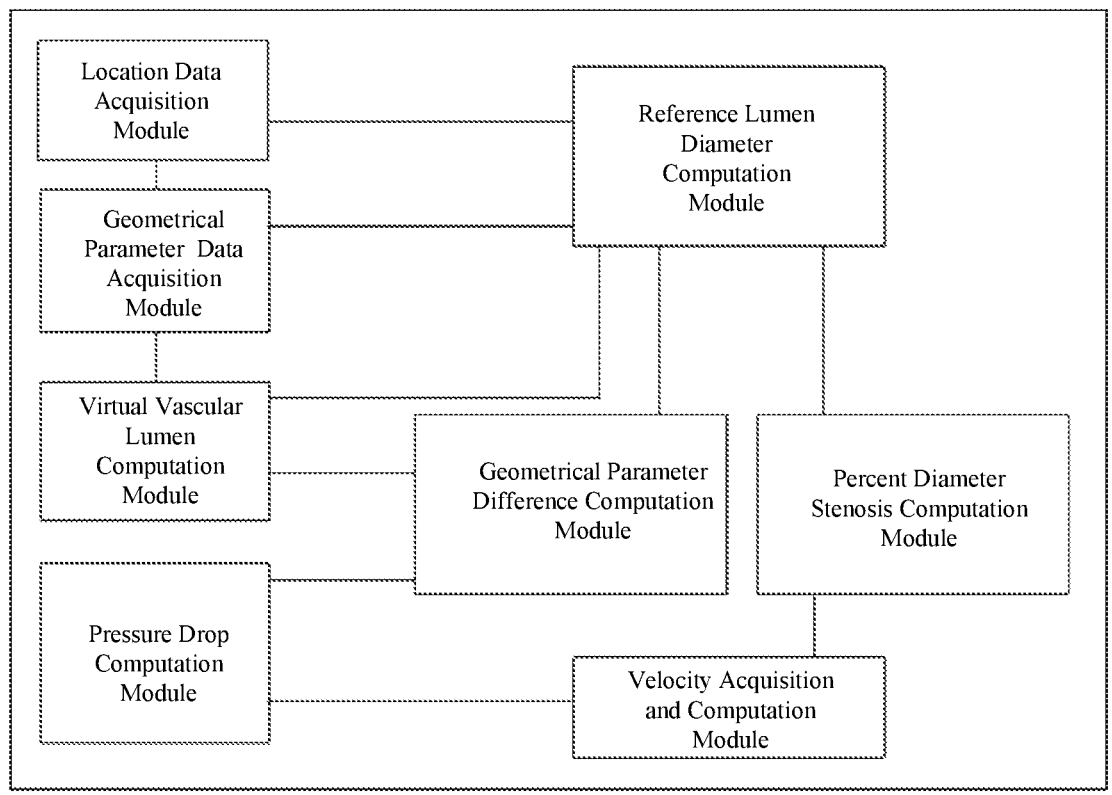
FIG. 4 is a schematic diagram of blood pressure drop system after implanting a virtual stent of the present invention.

As shown in FIGS. 3A and 3B, in the greater scale $\Delta h_1$, $F(X+\Delta h_1)-F(X)$ is nearly zero at focal lesions A, B. Therefore, f1(x) can reflect a geometrical parameter difference between an actual lumen diameter and a reference lumen diameter caused by long severe stenosis, with any geometrical parameter difference caused by focal stenosis being ignored. In the smaller scale $\Delta h_2$, geometrical parameter differences attributed to the focal stenosis A, B and the long stenosis C can be all identified. However, according to the derivative difference function f2(x) in the smaller scale, the derivatives of different severity of stenosis are substantially equal and cannot be used to distinguish the impacts of different severity of stenosis on the pressure deviation. To achieve this, it is contemplated to weighting the derivative difference functions f1(x) and f2(x) in the two scales.

Note that reference can be made to Patent Application No. CN201510901329.X, filed on Dec. 8, 2015, entitled "Method And System For Calculating Blood Vessel Pressure Difference And Fractional Flow Reserve (FFR)" for details in the computation in the multiple scales.

Embodiment 2

The present invention also provides a method of estimating post-virtual stenting fractional flow reserve (FFR) of a blood vessel, comprising: obtaining a pre-virtual stenting mean blood flow velocity V of a blood vessel segment in a resting state, optionally by conventional angiography (without maximum dilation of the microcirculation); calculating a pre-virtual stenting maximum blood flow velocity $V_{max}$ under the condition of maximum dilation of microcirculation based on the mean velocity V; obtaining a post-virtual stenting maximum blood flow velocity $V'_{max}$ by looking up a table listing relative blood flow velocities and their corresponding percent diameter stenosis based on the pre-virtual stenting maximum blood flow velocity $V_{max}$ and pre- and post-virtual stenting percent diameter stenosis, wherein the relative blood flow velocities are normalized by blood flow velocity, with a maximum value of 1 and a minimum value of 0, independent of patient's specific blood flow velocity value; computing a pressure drop $\Delta P_{max}$ corresponding to the post-virtual stenting maximum blood flow velocity $V'_{max}$; and computing post-virtual stenting FFR according to FFR=$(P1-\Delta P_{max})/P1$, where P1 represents a first blood flow pressure at a proximal end of a blood vessel segment, which can be approximately estimated from the cardiac diastolic and systolic pressures or accurately measured using a catheter.

Preferably, the maximum pre-virtual stenting blood flow velocity is obtained by looking up a correspondence table listing mean coronary blood flow velocities under a resting state and the corresponding maximum blood flow velocities at maximum dilation of microcirculation.

Preferably, the pressure drop $\Delta P_{max}$ corresponding to the maximum blood flow velocity is obtained by using the method of Embodiment 1.

Preferably, FFR is computed for a given fixed maximum blood flow velocity $V_{max}$.

Embodiment 3

In a specific embodiment, the present invention provides a system for estimating a post-virtual stenting pressure drop within a blood vessel, which can implement the method for computing a post-virtual stenting pressure drop set forth in the above embodiment. The system comprises: a geometrical parameter data acquisition module, configured to acquire geometrical parameters of a blood vessel segment, the blood vessel comprising a proximal end and a distal end, the geometrical parameters comprising a first geometrical parameter representing a cross-sectional area or diameter of the segment at the proximal end, a second geometrical parameter representing a cross-sectional area or diameter of the segment at the distal end and a third geometrical parameter representing a pre-virtual stenting cross-sectional area or diameter of an actual lumen of the segment at a first location between the proximal end and the distal end of the segment; a location data acquisition module, configured to acquire location data related to the first location; a reference lumen diameter computation module, configured to compute a reference lumen diameter of the segment at the first location based on the first geometrical parameter, the second geometrical parameter, the third geometrical parameter and the location data related to the first location; a virtual vascular lumen computation module, configured to receive a virtual stenting location and compute a fourth geometrical parameter as a geometrical parameter of virtual lumen of the post-virtually stented segment based on the third geometrical parameter and the reference lumen diameter, and wherein the fourth geometrical parameter representing a post-virtual stenting cross-sectional area or diameter of the segment at the first location between the proximal end and the distal end; a percent diameter stenosis computation module, configured to compute a pre-virtual stenting percent diameter stenosis at the first location based on the third geometrical parameter and the reference lumen diameter at the first location and compute a post-virtual stenting percent diameter stenosis at the first location based on the fourth geometrical parameter and the reference lumen diameter at the first location; a geometrical parameter difference computation module, configured to compute a geometrical parameter difference between the fourth geometrical parameter and the reference lumen diameter at the first location after virtual stenting; a velocity acquisition and computation module, configured to obtain a pre-virtual stenting mean blood flow velocity of the segment and obtain a post-virtual stenting mean blood flow velocity by looking up a table listing relative blood flow velocities and percent diameter stenosis; and a pressure drop computation module, configured to obtain the post-virtual stenting geometrical parameter difference at the first location output from the geometrical parameter difference computation module and the post-virtual stenting mean blood flow velocity and its square from the velocity acquisition and computation module to compute the post-virtual stenting pressure drop $\Delta P$ between a first blood flow pressure at the proximal end and a second blood flow pressure at the first location.

In a specific embodiment, the reference lumen diameter computation module is configured to derive a reference lumen diameter function based on the first geometrical parameter, the second geometrical parameter and a distance x from a certain position along the segment of vessel to the proximal end as a reference point, wherein the reference lumen diameter function is used to represent reference lumen diameter of different positions along the blood vessel as a function of the distance x between the position and the reference point.

In a specific embodiment, the system further comprises a normalization module configured to perform linear normalization as a function of location parameters within the range from the proximal end to the distal end of the vessel segment.

In a specific embodiment, the percent diameter stenosis corresponds to the most severe stenosis in the blood vessel segment.

In a specific embodiment, the geometrical parameter difference computation module is configured to derive geometrical parameter difference function at the first location after the virtual stenting based on the fourth geometrical parameter and the reference lumen diameter at the first location. The geometrical parameter difference function indicates a relationship of differences between the reference lumen diameter function and the geometrical parameter of the virtual lumen of the segment with respect to the distances x to the proximal end as a reference point.

In a specific embodiment, the system further comprises a multi-scale derivative difference computation module configured to compute derivatives of the post-virtual stenting geometrical parameter difference function in multiple scales.

In a specific embodiment, the pressure drop computation module is configured to compute the post-virtual stenting pressure drop $\Delta P$ between the first blood flow pressure and the second blood flow pressure by weighting integrals of the multiple scales of derivative difference functions based on the output of the multi-scale difference derivative computation module as well as the post-virtual stenting mean blood flow velocity V and its square $V^2$ output from the velocity acquisition and computation module, wherein the multiple scales comprise two or more scales implemented as resolutions indicative of distances between two adjacent points when calculating derivative numerically.

In a specific embodiment, the system further comprises a two-dimensional coronary angiography module configured to capture two-dimensional coronary angiography images of the segment under a certain angle and register region of interest of the images for different frames, wherein region of interest of the coronary angiography is from the proximal end of the segment to the distal end.

In a specific embodiment, the velocity acquisition and computation module is configured to plot a gray-level histogram from the registered region of interest based on the output from the two-dimensional coronary angiography module, and to fit the gray-level as a function of time within a cardiac cycle, based on which a pre-virtual stenting mean flow velocity of contrast medium within the segment of the vessel is obtained. A post-virtual stenting mean blood flow velocity is obtained through looking up the relative blood flow velocities and percent diameter stenosis.

In a specific embodiment, the table lists percent diameter stenosis and their corresponding relative blood flow velocities and is stored on the mean blood flow velocity acquisition and computation module or a separate storage module in the system. The relative blood flow velocities are normalized by blood flow velocity, with a maximum value of 1 and a minimum value of 0, independent of patient's specific blood flow velocity value.

Embodiment 4

In a further specific embodiment, the present invention provides a system of estimating post-virtual stenting fractional flow reserve (FFR) in a blood vessel, which can implement the method for computing a post-virtual stenting FFR set forth in the foregoing embodiment. The system comprises: a geometrical parameter data acquisition module, configured to acquire geometrical parameters of a blood vessel segment, the blood vessel comprising a proximal end and a distal end, the geometrical parameters comprising a first geometrical parameter representing a cross-sectional area or diameter of the segment at the proximal end, a second geometrical parameter representing a cross-sectional area or diameter of the segment at the distal end and a third geometrical parameter representing a pre-virtual stenting cross-sectional area or diameter of the segment at a first location between the proximal end and the distal end of the segment; a location data acquisition module, configured to acquire location data related to the first location; a reference lumen diameter computation module, configured to derive a reference lumen diameter function based on the geometrical parameters and a distance from a position on the segment to the proximal end, which is taken as a reference point; a virtual vascular lumen computation module, configured to receive a virtual stenting location and compute a fourth geometrical parameter as a virtual vascular geometrical parameter of virtual lumen of the post virtually stented segment based on the third geometrical parameter and the reference lumen diameter function, and wherein the fourth geometrical parameter representing a post-virtual stenting cross-sectional area or diameter of the segment at the first location between the proximal end and the distal end; a percent diameter stenosis computation module, configured to compute a pre-virtual stenting percent diameter stenosis at the first location based on the third geometrical parameter and the reference lumen diameter at the first location and compute a post-virtual stenting percent diameter stenosis at the first location based on the fourth geometrical parameter and the reference lumen diameter at the first location; a geometrical parameter difference computation module, configured to derive a geometrical parameter difference function of the post virtually stented segment based on the reference lumen diameter function and the fourth geometrical parameter; a multi-scale computation module, configured to compute derivatives of the post-virtual stenting geometrical parameter difference function in multiple scales, wherein the scales are resolutions indicative of distances between two adjacent points when calculating derivative numerically; a mean blood flow velocity acquisition and computation module, configured to acquire a mean blood flow velocity of the segment through conventional coronary angiography and obtain a post-virtual stenting mean blood flow velocity through looking up a table listing relative blood flow velocities and percent diameter stenosis; a maximum mean blood flow velocity computation module, configured to obtain a post-virtual stenting maximum mean blood flow velocity of the segment by looking up a correspondence table stored on this module; and an FFR computation module, configured to obtain post-virtual stenting FFR as a ratio of a second blood flow pressure at the first location to a first blood flow pressure at the proximal end of the segment based on the post-virtual stenting multi-scale derivative difference functions and the maximum mean blood flow velocity.

In a specific embodiment, the table lists percent diameter stenosis and their corresponding relative blood flow velocities and is stored on the mean blood flow velocity acquisition and computation module or a separate storage module in the system. The relative blood flow velocities are normalized by blood flow velocity, with a maximum value of 1 and a minimum value of 0, independent of patient's specific blood flow velocity value.

In a specific embodiment, the maximum blood flow velocity acquisition module is configured to obtain the maximum blood flow velocity by looking up the correspondence table listing mean coronary blood flow velocities under a resting state and the corresponding maximum blood flow velocities at maximum dilation of microcirculation. The correspondence table is stored on the maximum blood flow velocity acquisition module or a separate storage module in the system.

It is to be noted that the above systems and functional modules are presented merely as an example to describe a basic, but not the only, structure for implementing the present invention.

Persons of ordinary skill in the art can understand all or part of the processes of the methods according to the foregoing embodiments, which can be implemented by hardware under the instruction of a computer program. The program can be stored on a computer-readable storage medium. When executed, the program can implement the processes of the methods according to the embodiments. The storage medium can be a magnetic disk, a CD-ROM, a read-only memory (ROM), a random access memory (RAM) or the like.

While the invention has been described with reference to several preferred embodiments, it is not intended to be limited to these embodiments in any sense. Various changes and modifications may be easily conceived by any person of skill in the art within the scope of the above teachings of the invention. Accordingly, the scope of the invention shall be as defined in the appended claims.

What is claimed is:

1. A method for estimating post-virtual stenting pressure drop within a blood vessel segment, comprising:

receiving geometrical parameters of a blood vessel segment comprising a proximal end and a distal end, wherein the geometrical parameters comprises a first geometrical parameter representing a cross-sectional area or diameter of the proximal end of the segment, a second geometrical parameter representing a cross-sectional area or diameter of the distal end of the segment, and a third geometrical parameter representing a cross-sectional area or diameter of a pre-virtual stenting actual lumen of the segment at a first location between the proximal end and the distal end;

computing a reference lumen diameter at the first location of the segment based on the first geometrical parameter, the second geometrical parameter, the third geometrical parameter and a location data related to the first location;

receiving a virtual stenting location defined by distances from proximal and distal ends of the virtual stent to the proximal end of the segment;

computing a fourth geometrical parameter of a virtual lumen of a post virtually stented segment based on the third geometrical parameter, the virtual stenting location and the reference lumen diameter at the first location, the fourth geometrical parameter representing a cross-sectional area or diameter of the post virtually stented segment at the first location between the proximal end and the distal end;

receiving a pre-virtual stenting mean blood flow velocity of the segment;

computing a pre-virtual stenting percent diameter stenosis at the first location based on the third geometrical parameter and the reference lumen diameter at the first location; computing a post-virtual stenting percent diameter stenosis and a post-virtual geometrical parameter difference at the first location based on the fourth geometrical parameter and the reference lumen diameter at the first location;

obtaining a post-virtual stenting mean blood flow velocity by looking up a table listing relative blood flow velocities with respect to percent diameter stenosis based on the pre-virtual stenting mean blood flow velocity and the pre- and post-virtual stenting percent diameter stenosis;

computing a post-virtual stenting pressure drop $\Delta P$ between a first blood flow pressure at the proximal end and a second blood flow pressure at the first location based on the post-virtual geometrical parameter difference at the first location, the post-virtual stenting mean blood flow velocity V and its square $V^2$.

2. The method of claim 1, further comprising:
with the proximal end as a reference point, deriving a reference lumen diameter function based on the first geometrical parameter, the second geometrical parameter and a distance x from a certain position along the segment to the reference point, wherein the reference lumen diameter function represents reference lumen diameter at different positions along the segment as a function of the distance x from the position to the reference point.

3. The method of claim 2, wherein the derivation of the reference lumen diameter function comprises a linear normalization as a function of location from the proximal end to the distal end of the segment.

4. The method of claim 2, wherein computing the fourth geometrical parameter of the post-virtually stented segment by replacing the third geometrical parameter with the reference lumen diameter according to the virtual stenting location, taking the proximal end as a reference point.

5. The method of claim 4, further comprising:
with the proximal end as a reference point and based on the fourth geometrical parameter and the reference lumen diameter function, deriving a post-virtual stenting geometrical parameter difference function of the segment which indicates a relationship of differences between the reference lumen diameter function and the fourth geometrical parameter with respect to the distances x from the reference point.

6. The method of claim 4, further comprising:
computing the pre-virtual stenting percent diameter stenosis DS % based on the third geometrical parameter and the reference lumen diameter function and computing the post-virtual stenting percent diameter stenosis DS %' based on the fourth geometrical parameter and the reference lumen diameter function.

7. The method of claim 6, further comprising:
obtaining the post-virtual stenting mean blood flow velocity V' by looking up the table listing relative blood flow velocities and their corresponding percent diameter stenosis based on the pre-virtual stenting mean blood flow velocity V and the pre- and post-virtual stenting percent diameter stenosis DS %, DS %'.

8. The method of claim7, wherein the table lists percent diameter stenosis with respect to relative blood flow velocities, and wherein the relative blood flow velocities are normalized by blood flow velocity, with a maximum value of 1 and a minimum value of 0.

9. The method of claim 4, further comprising:
computing derivatives of a post-virtual stenting geometrical parameter difference function in n scales f1(x), . . . , fn(x), wherein the post-virtual stenting pressure drop $\Delta P$ between the first blood flow pressure and the second blood flow pressure is computed based on the n scales of derivative difference functions, wherein n is a natural number greater than 1, and wherein the scales are resolutions indicative of distances between two adjacent points when calculating derivative numerically.

10. The method of claim 9, further comprising:
the post-virtual stenting pressure drop $\Delta P$ between the first blood flow pressure and the second blood flow pressure is calculated by weighting integrals of n scales of the derivative difference functions f1(x), . . . , fn(x), and based on the post-virtual stenting mean blood flow velocity V and its square $V^2$.

11. The method of claim 10, further comprising:
computing the post-virtual stenting pressure drop $\Delta P$ between the first blood flow pressure and the second blood flow pressure according to:

$$\Delta P = \alpha_1[C_1V+C_2V^2]*\!\int\! f_1(x)dx + \alpha_2[C_1V+C_2V^2]\!\int\! f_2(x)dx + \ldots + \alpha_n[C_1V+C_2V^2]*\!\int\! f_n(x)dx$$

where $C_1$ and $C_2$ represent coefficients of the post-virtual stenting mean blood flow velocity V and its square $V^2$, respectively, and $\alpha_1, \alpha_2, \ldots,$ and $\alpha_n$ denote weighted coefficients of the derivative difference functions f1(x), f2(x), . . . , fn(x) in the n scales, respectively.

12. The method of claim 1, wherein the location data related to the first location is a distance from the first location to the proximal end of the segment, and wherein the mean blood flow velocity is a mean blood flow velocity within the proximal end to the distal end of the segment.

13. The method of claim 1, further comprising: receiving two-dimensional coronary angiography images under a certain angle; and
registering region of interest of the images for different frames, wherein the region of interest of the coronary angiography is from the proximal end of the segment to the distal end.

14. The method of claim 13, further comprising: plotting a gray-level histogram from the registered region of interest; and fitting the gray-level as a function of time within a cardiac cycle.

15. The method of claim 14, further comprising: obtaining a mean flow velocity of contrast medium within the segment from the gray-level fitting function.

16. The method of claim 15, wherein the pre-virtual stenting mean blood flow velocity V of the segment is approximately equal to the mean flow velocity of the contrast medium obtained from the gray-level fitting function.

17. A method for estimating post-virtual stenting fractional flow reserve (FFR) in a blood vessel segment, comprising:
receiving a pre-virtual stenting mean blood flow velocity V of a blood vessel segment in a resting state;
calculating a pre-virtual stenting maximum blood flow velocity $V_{max}$ under a condition of maximum dilation of microcirculation based on the mean blood flow velocity V;
obtaining a post-virtual stenting maximum blood flow velocity $V'_{max}$ by looking up a table listing relative blood flow velocities and their corresponding percent diameter stenosis based on the maximum blood flow velocity $V_{max}$ and pre- and post-virtual stenting percent diameter stenosis;
solving for a pressure drop $\Delta P_{max}$ corresponding to the post-virtual stenting maximum blood flow velocity $V'_{max}$; and
computing post-virtual stenting FFR according to FFR= $(P1-\Delta P_{max})/P1$, wherein P1 represents a first blood flow pressure at a proximal end of the segment.

18. The method of claim 17, further comprising:
obtaining the pre-virtual stenting maximum blood flow velocity by looking up a correspondence table listing mean coronary blood flow velocities in a resting state and a corresponding maximum blood flow velocities under the condition of maximum dilation of microcirculation.

19. The method of claim 17, further comprising:
obtaining the pressure deviation $\Delta P_{max}$ using the method as defined in claim 1.

* * * * *